(12) United States Patent
Malorni et al.

(10) Patent No.: US 8,210,403 B2
(45) Date of Patent: Jul. 3, 2012

(54) DISPENSER FOR DELIVERING MEDICAMENT

(75) Inventors: Sergio Malorni, Berkshire (GB); David John Marchant, Berkshire (GB)

(73) Assignee: Sosei R&D Ltd., Essex (GB)

( * ) Notice: Subject to any disclaimer, the term of this patent is extended or adjusted under 35 U.S.C. 154(b) by 1049 days.

(21) Appl. No.: 11/817,534

(22) PCT Filed: Mar. 13, 2006

(86) PCT No.: PCT/GB2006/000874
§ 371 (c)(1),
(2), (4) Date: May 20, 2008

(87) PCT Pub. No.: WO2006/095194
PCT Pub. Date: Sep. 14, 2006

(65) Prior Publication Data
US 2009/0120962 A1    May 14, 2009

(30) Foreign Application Priority Data
Mar. 11, 2005   (GB) .................................. 0505058.8

(51) Int. Cl.
*G04C 23/00* (2006.01)
(52) U.S. Cl. .............. 222/648; 222/153.04; 222/153.11; 222/153.14; 222/1
(58) Field of Classification Search ............ 222/153.11, 222/153.13, 153.14, 402.11, 402.14, 156, 222/159, 644–647, 43, 644–64, 438, 1
See application file for complete search history.

(56) References Cited

U.S. PATENT DOCUMENTS

| | | | |
|---|---|---|---|
| 5,855,297 A * | 1/1999 | Tichenor et al. | ................ 222/61 |
| 6,454,185 B2 | 9/2002 | Fuchs | |
| 6,929,154 B2 * | 8/2005 | Grey et al. | ............... 222/153.03 |
| 2002/0000225 A1 | 1/2002 | Schuler et al. | |
| 2003/0099158 A1 | 5/2003 | De la Huerga | |
| 2004/0069798 A1 | 4/2004 | Grey et al. | |

FOREIGN PATENT DOCUMENTS

| | | |
|---|---|---|
| CH | 647 656 A5 | 2/1985 |
| JP | 05042979 A * | 2/1993 |
| WO | WO 92/07599 A1 | 5/1992 |
| WO | WO 00/78639 A1 | 12/2000 |
| WO | WO 03/097141 A2 | 11/2003 |
| WO | WO 2004/062717 A1 | 7/2004 |
| WO | WO 2004/071562 A1 | 8/2004 |

* cited by examiner

*Primary Examiner* — Kevin P Shaver
*Assistant Examiner* — Melvin Cartagena
(74) *Attorney, Agent, or Firm* — Saliwanchik, Lloyd & Eisenschenk

(57) ABSTRACT

A method for the vaporization of particulate material (10) includes providing one or more containers (15) each containing possibly distinct particulate materials (10) each having at least one component, fluidizing the particulate material (10) in at least one of the containers (15), and providing a vaporization zone (50) that is thermally isolated from at least one of the containers (15). The method further includes delivering particulate material received from each container (15) to the vaporization zone (50), and applying heat to vaporize the delivered particulate materials (10) at the vaporization zone (50).

29 Claims, 15 Drawing Sheets

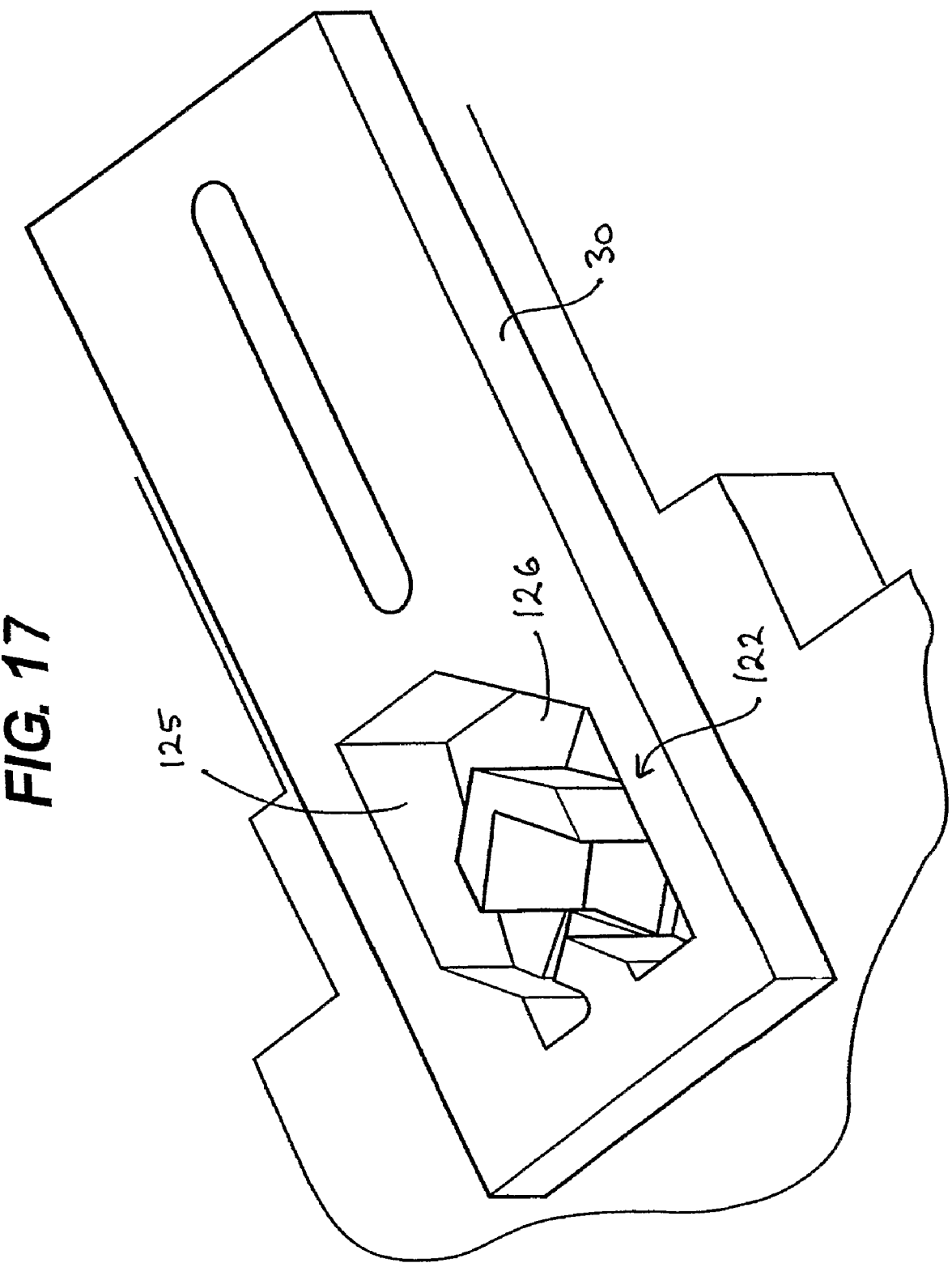

DISPENSER FOR DELIVERING MEDICAMENT

This application is a National Stage Application of International Application Number PCT/GB2006/000874, filed Mar. 13, 2006; which claims priority to Great Britain Application No. 0505058.8, filed Mar. 11, 2005.

FIELD OF THE INVENTION

This invention relates to dispensing systems for use in patient care and in particular but not exclusively to dispensing metered doses of medicinal or therapeutic products. One aspect of the invention relates to a dispensing system for sublingual delivery of a pain-relieving drug, but other applications of the invention relate to other fields such as inhalation delivery.

BACKGROUND OF THE INVENTION

There are many different dispensers which are utilised to dispense a metered dose of a product such that the dose can be self-administered, by the patient, under the direction of a physician, such dispensers including primarily aerosol dispensers relying upon a pressurised dispensing container having a metering valve and pump dispensers having a pump chamber arranged to dispense a metered dose. It is important to regulate use of the dispenser, to avoid overdosing where the product is a potentially dangerous or expensive drug.

Lock-out mechanisms have been disclosed, for example in U.S. Pat. No. 4,934,358, for preventing actuation of an inhalation dispenser other than in accordance with a predetermined dosing schedule. Similarly, GB2368061A discloses a locking mechanism to prevent further dispensing until electronically released in accordance with a desired dispensing program.

It is also known from WO03/097141, for a dispensing system to be provided with a control circuit which can be programmed to provide a dosing regime in accordance with the requirements of a physician.

SUMMARY OF THE INVENTION

The present invention seeks to provide improvements in such dispensing systems with a view to providing a practical solution in a marketable product. It can be used, for example, to dispense a formulation of a drug such as fentanyl, as described in WO2004/080382.

In one aspect of the invention, a dispenser includes a lock having a resilient self-locking mechanism for placing the lock into a locked state after each dose is dispensed. A sensor is provided to sense when the lock is in this locked state and a control circuit is responsive to the sensor and operable after a lock-out period to energise a lock actuator to return the lock to an unlocked state.

In another aspect, a lock is included with first and second retaining means that are operable independently of a lock actuation, so that the actuator requires to be engaged only when changing the lock from the locked to the unlocked state, or vice versa.

In a preferred embodiment, a push-push mechanism enables the lock to be responsive to the control circuit for both locking and unlocking, in addition to constituting the resilient self-locking mechanism.

DESCRIPTION OF THE DRAWINGS

FIG. 17 is a perspective view showing a cam track of the push-push mechanism.

DESCRIPTION OF PREFERRED EMBODIMENTS

Embodiments of the present invention will now be described by way of example only and with reference to the accompanying drawings.

Figure 1:
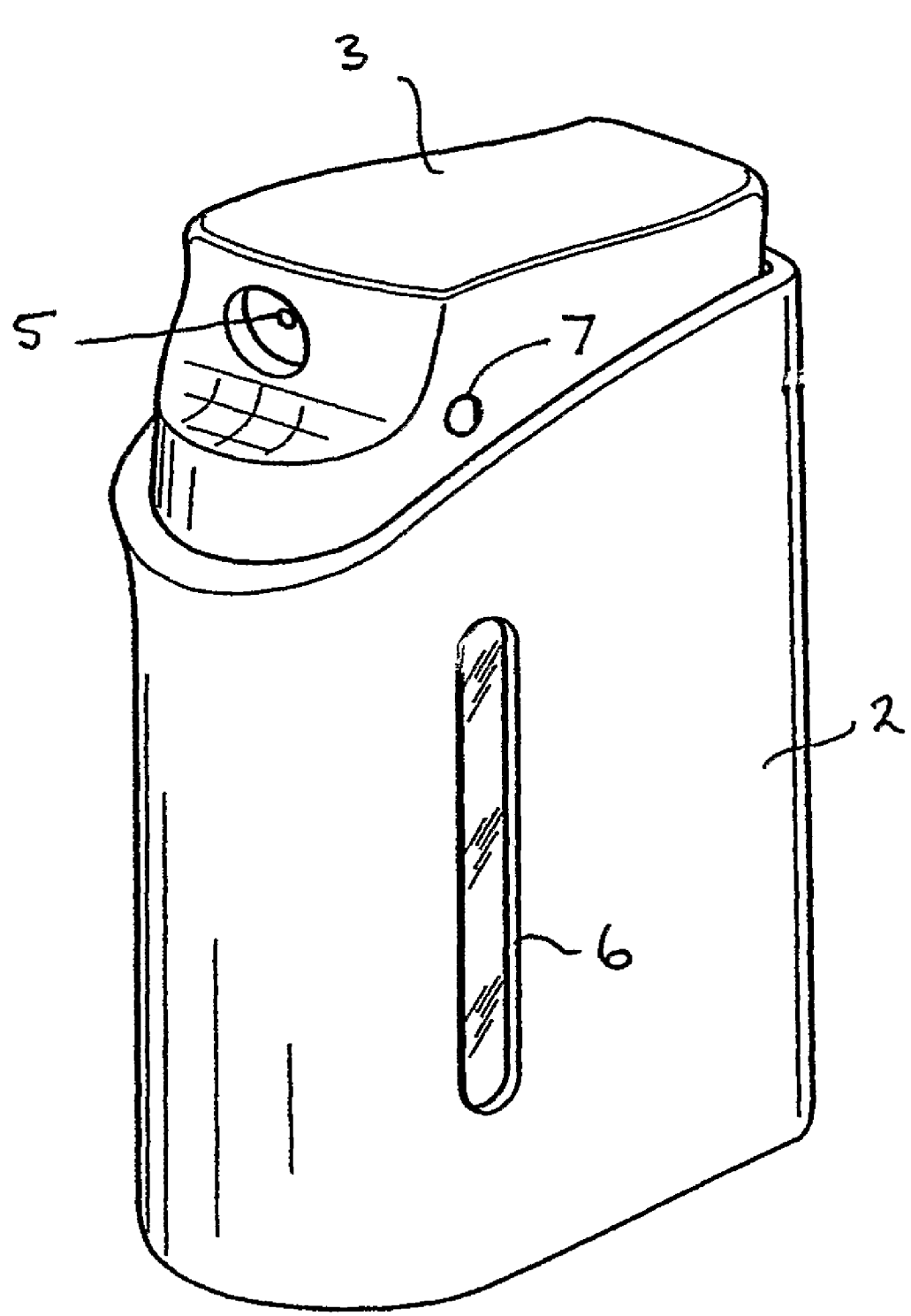
FIG. 1 is a perspective external view of a dispenser.

The embodiment of FIG. 1 comprises a dispensing system 1 suitable for sublingual delivery of a narcotic product for use in pain relief. A housing 2 is closed at its upper end by a button 3 which can be manually depressed relative to the housing by a user wishing to dispense a dose of a product held in a container. The button 3 is located above the container, and is constrained from being removed from the housing by internal stop features. The button 3 also defines an aperture through which a dispensing nozzle 5 delivers an aerosol spray of product.

A window 6 is formed in the housing 2, through which the presence and/or amount of product in the container can be inspected. The button 3 includes a port 7 through which an indicator for verifying the current status of an internal lock can be viewed. A removable dust cap may be provided so as to clip onto the housing in a manner which shields the button from the ingress of debris prior to use.

The shape and size of the viewing window 6 may be varied, e.g. depending on the length of the container.

Figure 2:
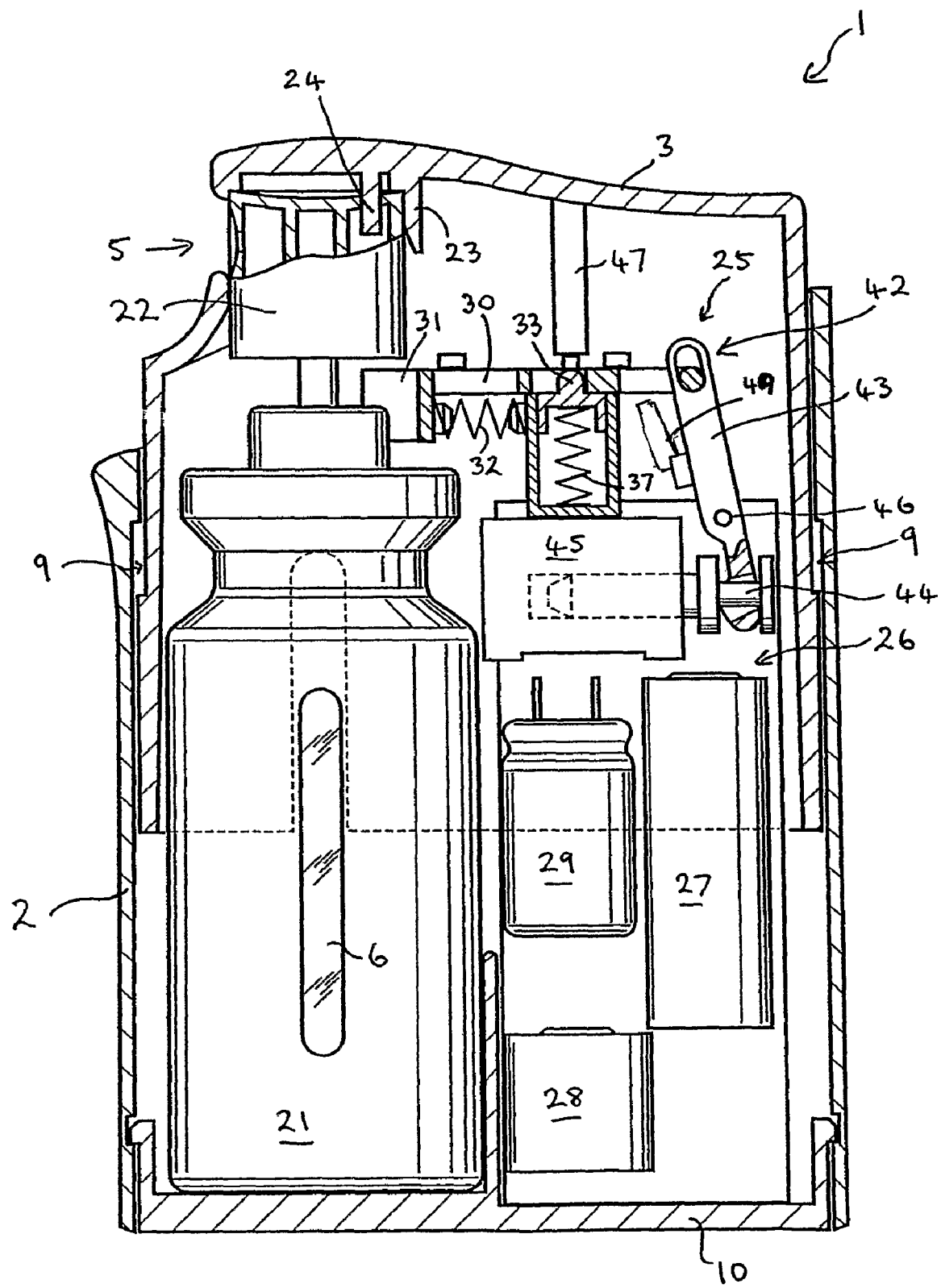
FIG. 2 is a sectional elevation of a dispensing system in accordance with a first embodiment, in which an actuator is in a rest position and the system includes a lock which is in an unlocked state.

FIG. 2 shows the internal construction of the dispensing system 1, including a glass-walled container 21 and an actuator 22 for delivering an aerosol spray through dispensing nozzle 5 when the actuator is depressed. The button 3 is located on the actuator 22 by protrusions 23 and 24, the actuator having a generally cylindrical outer surface engaged peripherally by the protrusion 23 and an aperture located by the protrusion 24. Depressing the button 3 relative to the housing 2 causes depression of the actuator, along the longitudinal axis of the container to provide a dispensing stroke of the dispenser. The location of the protrusion 24 in an aperture formed in the upper end of the actuator 22 prevents misalignment of the actuator relative to the button 3, thereby maintaining the dispensing nozzle 5 in alignment with the opening defined by the applicator 4, to ensure unimpeded delivery.

The button 3 is prevented from being removed from the housing by cooperating stop formations 9. The housing 2 includes a chassis 10 connected by snap-fit connectors to side wall portions of the housing.

The dispenser also includes a lock 25 for selectively preventing actuation of the actuator 22 and a control circuit 26 for electrically releasing the lock 25.

FIG. 2 shows also a primary battery 27 for energising the lock and a secondary battery 28 for the operation of the control circuit 26, and a capacitor 29.

The lock 25 comprises a locking member 30 which is slidable in a direction normal to the direction of depression of the actuator, so as to be movable into and out of a locking position in which an end portion 31 of the locking member limits travel of the actuator 22, to prevent completion of a dispensing stroke.

In FIG. 2, the locking member 30 is shown in a position in which the lock 25 is unlocked and the end portion 31 does not impede axial movement of the actuator 22.

Figure 3:
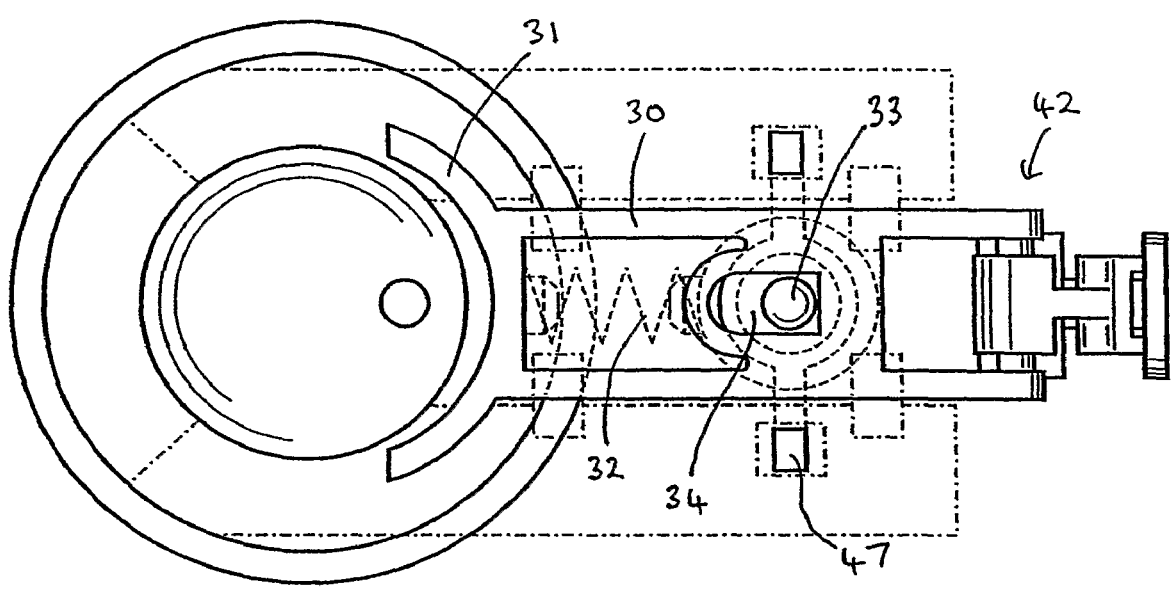
FIG. 3 is a plan view of the system of FIG. 2, illustrating components of the lock.

A spring 32 in the form of a compression coil spring biases the locking member 30 towards the actuator 22. When the lock 25 is in the unlocked state and the button 3 is in the rest position, as shown in FIG. 2, the locking member 30 is retained against action of the spring 32 by a latch 33 which, as shown more clearly in FIG. 3, projects into an aperture 34 formed in the locking member. The latch 33 comprises a domed head mounted on a cylindrical piston 35 which is slidable within a fixed cylinder 36 and upwardly biased by a second spring 37 into latching engagement with the locking member 30.

At its end 42 distant from the actuator 22, the locking member 30 is pivotally connected to one end of a lever 43 whose other end is connected to a plunger 44 of a pull solenoid 45. The lever 43 is pivoted about a pivot pin 46 located so as to apply a 2:1 leverage ratio, thereby amplifying movement applied to the locking member 30 by solenoid plunger 44. This amplified movement is applied to provide sliding motion of the locking member 30 when the solenoid 45 is energised. Since the solenoid 45 is a pull solenoid, energising the solenoid results in the plunger 44 being retracted within the solenoid and, by lever action, the locking member 30 being urged outwardly with respect to the actuator 22.

One leg or a pair of legs 47 project from the button 3 into abutment with the top surface of the latch 33 so that depression of the button 3 results in the latch 33 being pushed against action of the second spring 37 in a direction which retracts the domed head of the latch 33 from the aperture 34 and releases the locking member 30. As described below, this release occurs only after the actuator 22 has been depressed to a point beyond the limit of travel available when locked, so that the released locking member cannot yet advance fully to its locked position.

Electrical contact pins (not shown) are located in fixed positions adjacent to the lever 43 and are contactable by a resilient contact 49 mounted on the lever and arranged to make electrical contact between the pins whenever the lock 25 is in the locked state as described below.

Figure 4:
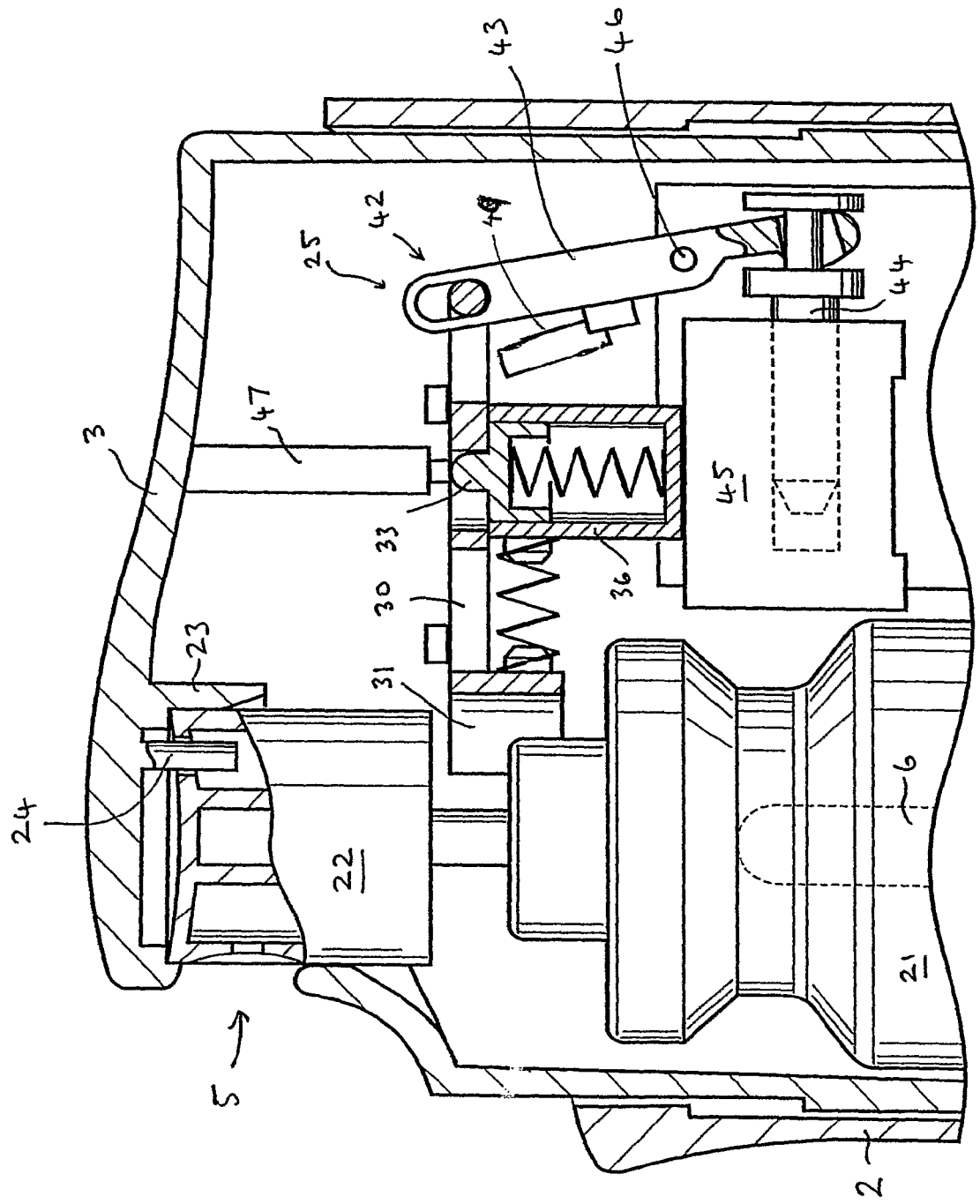
FIG. 4 is an enlarged elevation sectioned to show detail of FIG. 2.

FIG. 4 shows part of the dispenser in the same state as in FIG. 2. In this configuration, the lock 25 is in an unlocked state with the locking member 30 latched in a fully retracted position. The contact 49 is not touching the contact pins.

Figure 5:
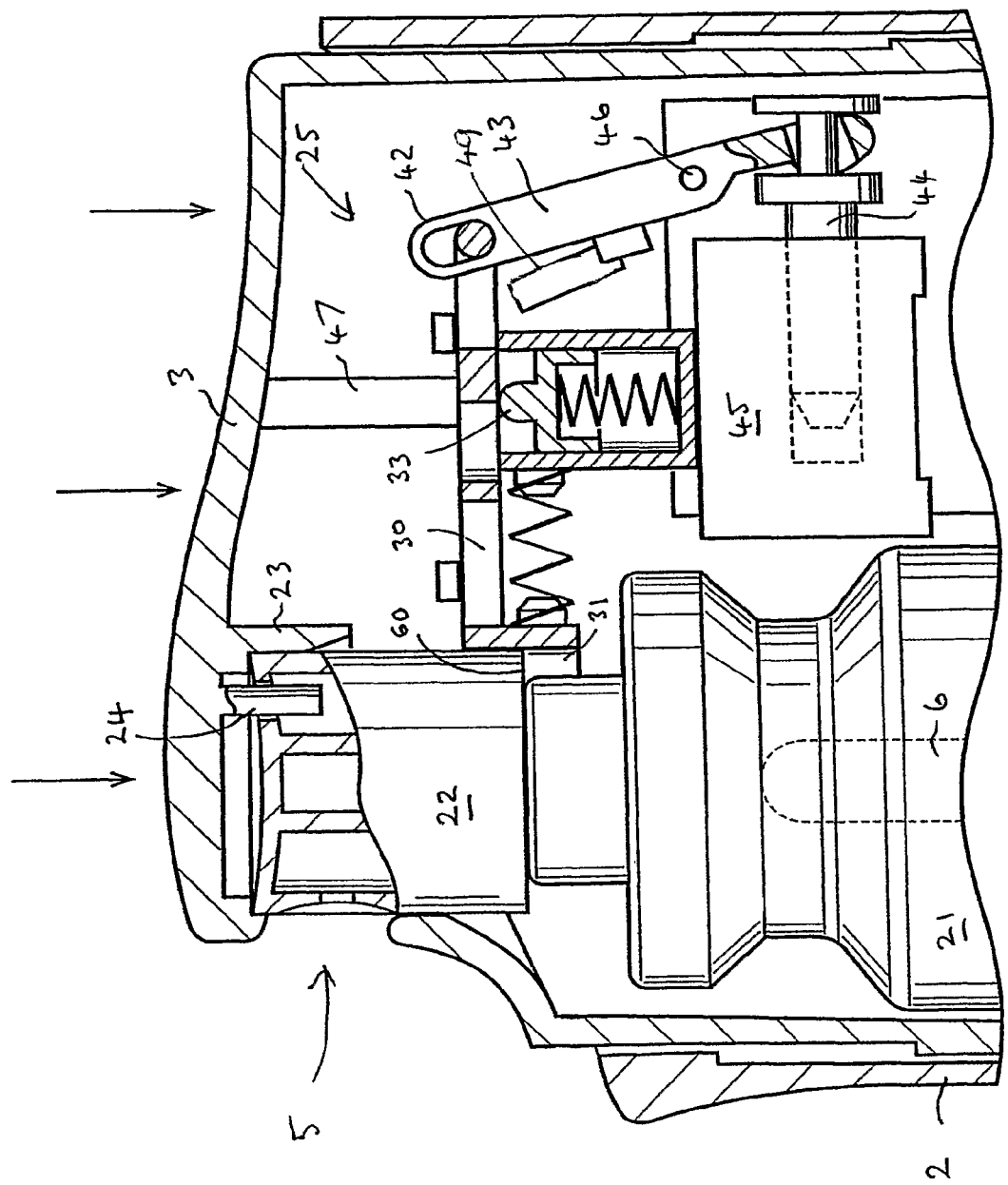
FIG. 5 is a view corresponding to FIG. 4, showing the actuator partially depressed and the lock primed for self-locking action.

FIG. 5 illustrates partial depression of the button 3, resulting in motion of the actuator 22 towards the container 21 to a position where a shoulder 60 defined by the actuator 22 is able to pass beyond the position of the locking member 30, while the locking member 30 is retained by action of the latch 33 from limiting travel of the actuator.

Having passed this position, the legs 47 depress the latch 33 to the point where the locking member is free to advance with a sliding motion towards the actuator 22 under action of the spring 33. This sliding motion eventually causes the locking member 33 to come into sliding contact with the cylindrical surface of the actuator 22 as the actuator continues to travel.

FIG. 5 therefore shows the lock 25 in an unlocked state but in which the locking member 30 is unlatched and therefore primed to provide self-locking action during the return stroke of the button 3 as described further below. The contact 49 is still not touching the contact pins.

Figure 6:
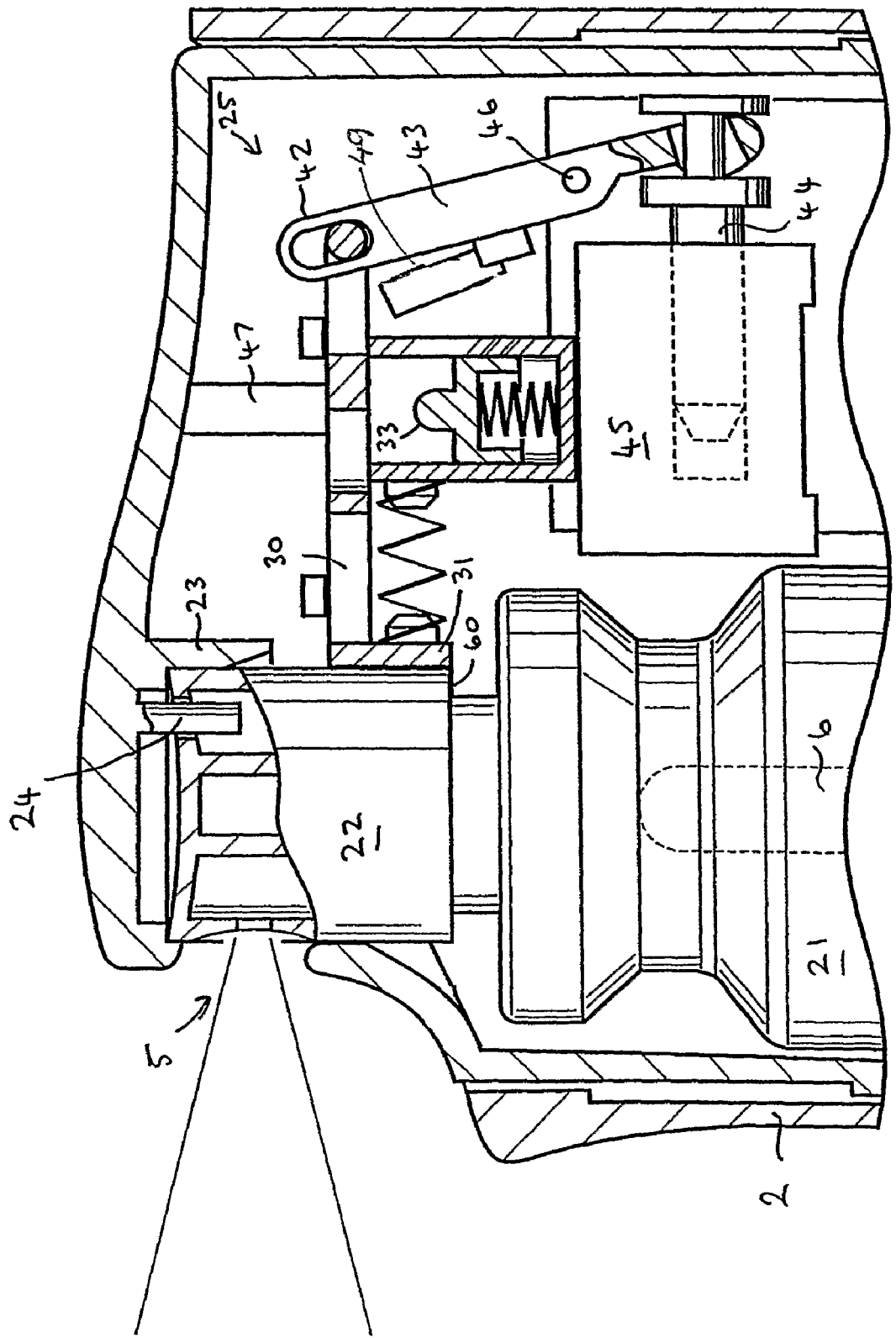
FIG. 6 is a view corresponding to FIG. 5, showing full depression of the actuator to release a dose.

FIG. 6 illustrates the position of the button at its maximum degree of travel, at which point the dispenser causes a dose of spray in aerosol form to be dispensed via the dispensing nozzle 5. The dispenser is of a type which can dispense only a single dose in response to one actuating displacement of the actuator 22 e.g., through a stroke of 6 mm. The initial portion of the travel, e.g. the first 2 mm of depression, does not produce spray output and constitutes a degree of over-travel in the movement of the actuator. Following the release of the metered dose, no further discharge is possible immediately. When the actuator 22 has been allowed to return to within the initial portion of travel from its rest position, as shown in FIG. 4, a further dispensing stroke may be completed depressing the actuator 22 to the position shown in FIG. 6.

In the fully depressed position shown in FIG. 6, the locking member 30 is still in sliding contact with the cylindrical surface of the actuator 22. The lock 25 therefore continues to be in an unlocked state, with the locking member primed ready for self-locking action. The contact 49 is still not touching the contact pins.

Figure 7:
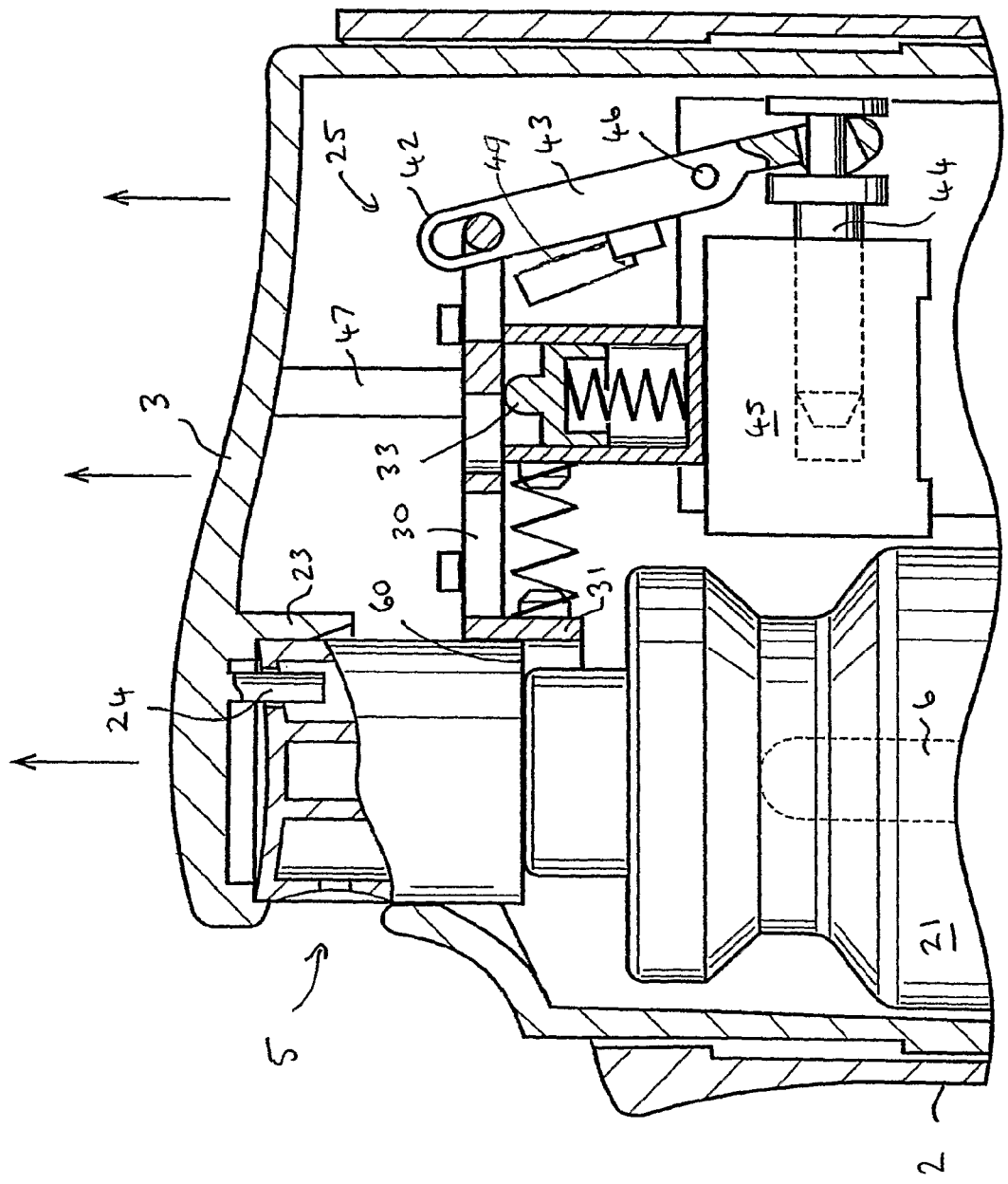
FIG. 7 is a view corresponding to FIG. 6, after partial release of the actuator.

FIG. 7 illustrates a further position in which the button 3 has been partially released and the button together with actuator 22 is in the process of returning to its rest position. This return stroke motion is achieved by the presence of a resilient mechanism within the container 21, which generally requires the presence of a coil spring biasing a valve stem on which the actuator is mounted into an extended position in which the actuator 22 is fully raised.

Figure 8:
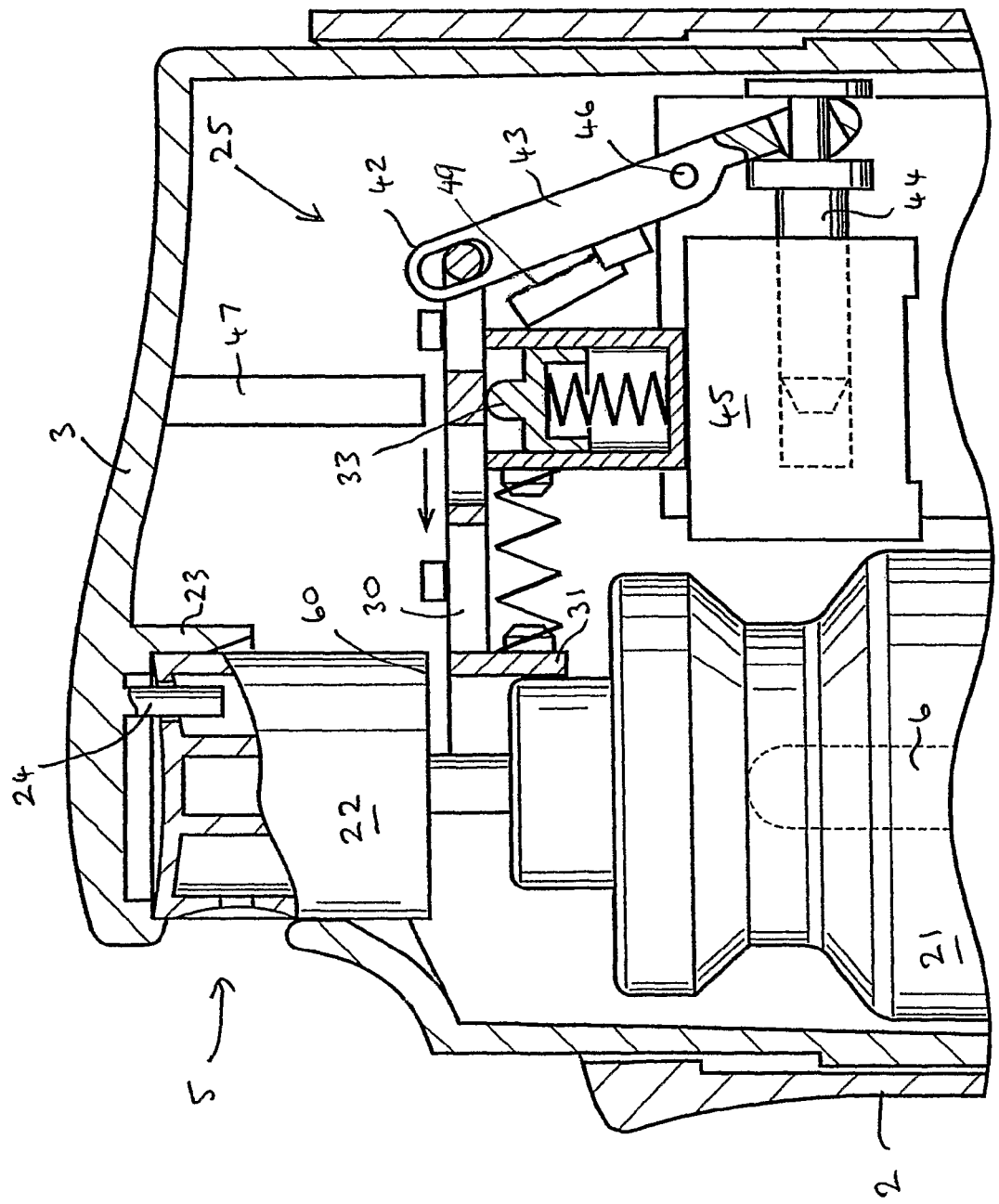
FIG. 8 is a view corresponding to FIG. 7, after the actuator has fully returned to its rest position and the lock has entered the locked state.

In FIG. 7, the locking member 30 maintains sliding contact with the cylindrical surface of the actuator 22 as the actuator progressively moves upwardly and away from the container 21. The position of the shoulder 60 eventually rises to a level where it clears the upper surface of the locking member 30 which then is able to travel under the influence of the spring 32 into a locking position as shown in FIG. 8. The contact 49 remains not touching the contact pins.

In FIG. 8 the end portion 31 of the locking member 30 extends inwardly of the shoulder 60. In this locked state, subsequent depression of the button 3 causes the shoulder 60 to engage axially the upper surface of the locking member 30 at the end portion 31 so that the locking member 30 will limit travel of the actuator and prevent the actuator from reaching a position where a further dose can be dispensed.

In the locked state as shown in FIG. 8, the lever 43 is tilted to a position where electrical contact is made between the contact pins and the contact 49 which thereby together provide a sensor to which the control circuit 26 is responsive. This change of status in the electrical condition of the sensor is interpreted by the control circuit 26 as indicating that a dose has been dispensed. In practice, the timing at which the sensor changes state will be momentarily after the instant at which the dose is dispensed since the lock 25 does not enter its locked state until part-way through the return stroke of the actuator 22. Since in practice the actuator 22 will be released immediately after the dispensing of a dose, this timing delay is acceptable.

Figure 9:
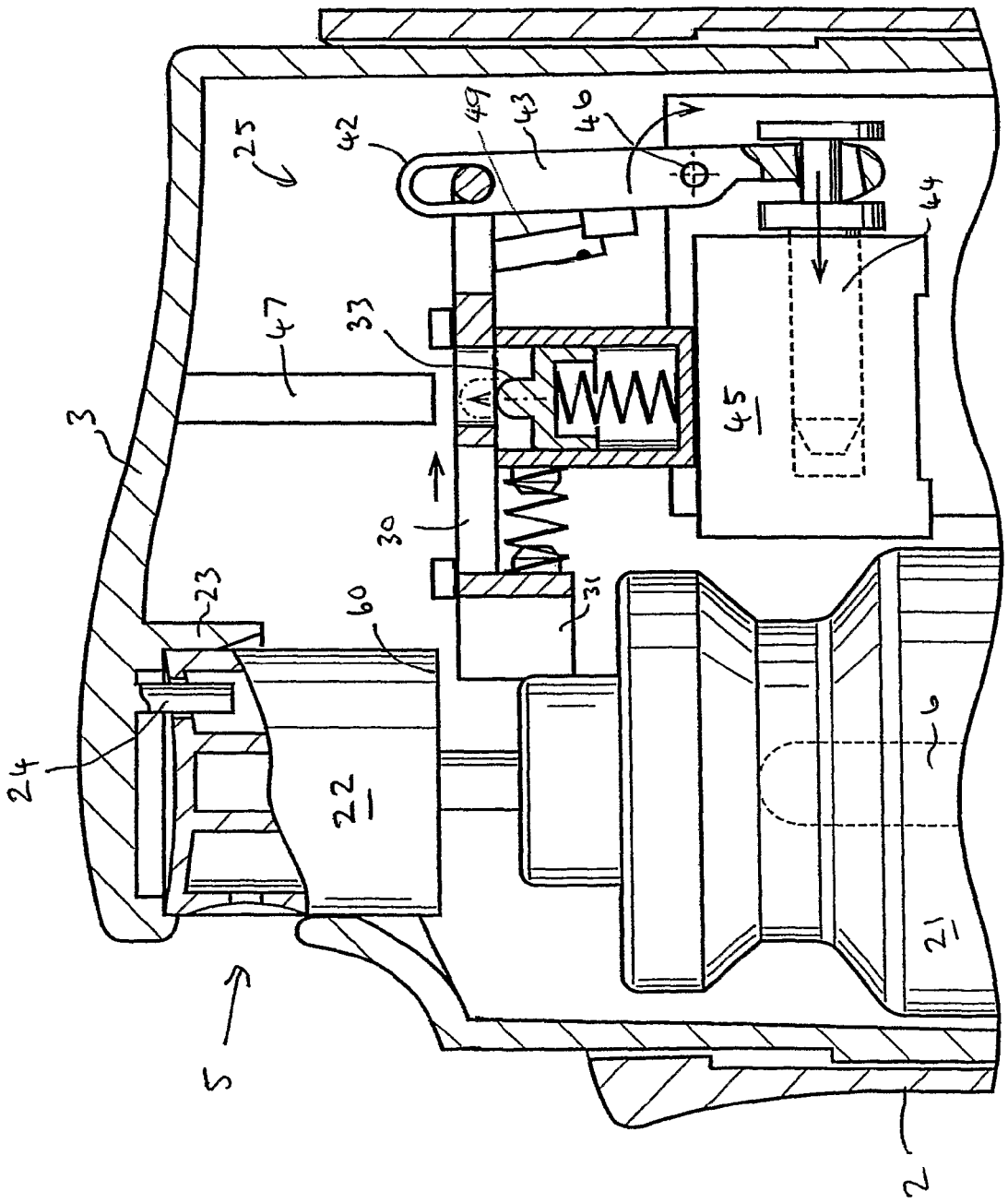
FIG. 9 is a further view of the embodiment of preceding figures, showing the energising of a lock actuator to return the lock to its unlocked state.

In the locked state of the dispensing system 1, no further dose may be dispensed. The control circuit 26 is configured to determine, by measuring elapsed time from entering the locked state, a further time at which the lock 25 can be released to allow a further dose to be dispensed. After such a lock-out period has elapsed, the control circuit 26 unlocks the lock 25 by energising the solenoid 45, thereby retracting the plunger 44 as shown in FIG. 9. This motion is communicated via the lever 43 to the locking member 30, causing the locking member to be retracted to the position shown in FIG. 9 at which the latch 33 can again engage the locking member. After engagement by the latch 33, the rest state shown in FIG. 4 is again achieved, and the lock 25 then remains in its unlocked state with the locking member 30 retracted to a position where its end portion 31 no longer limits travel of the actuator 22. A further dose may therefore be dispensed at any time. After the further dose, the lock 25 will again be self-locking, thereby triggering the measurement of a further lock-out period by the control circuit 26 before the lock is released. The control circuit may be configured to keep track of the number of doses dispensed, to compute the frequency with which doses are dispensed, and may be configured to regulate the length of the lock-out period accordingly, in order to comply with a prescribed dosing schedule.

In order to energise the solenoid 45, the control circuit 26 applies a charging voltage to the capacitor 29 and, after an appropriate charging period, connects the output voltage to the solenoid to deliver a current pulse for solenoid actuation. Since the locking member 30 is then retained by action of the latch 33, it is sufficient to energise the solenoid only during the transition from the locked to the unlocked state of the lock 25. The lock may thereafter be maintained in an unlocked state for an indefinite period without energy consumption. Similarly, the sensor draws current only when the lock 25 is in the locked state. However, since this will typically occur only during a lock-out period of no more than a few hours, e.g. one hour, the use of the sensor does not represent a continuous drain on the current resources of the control circuit 26. These features contribute to prolong the shelf-life of the system 1, typically of the order of 3 years.

A second embodiment will now be described. The second embodiment has a number of features in common with the first embodiment, for example the same overall appearance as shown in FIG. 1, and the same reference numerals will be used for internal components where corresponding or equivalent features are present. Detailed description of components in the second embodiment will be omitted where it is apparent that they correspond to features previously described with reference to the first embodiment so that parts of the description of the first embodiment may be assumed to be incorporated where appropriate.

Figure 10:
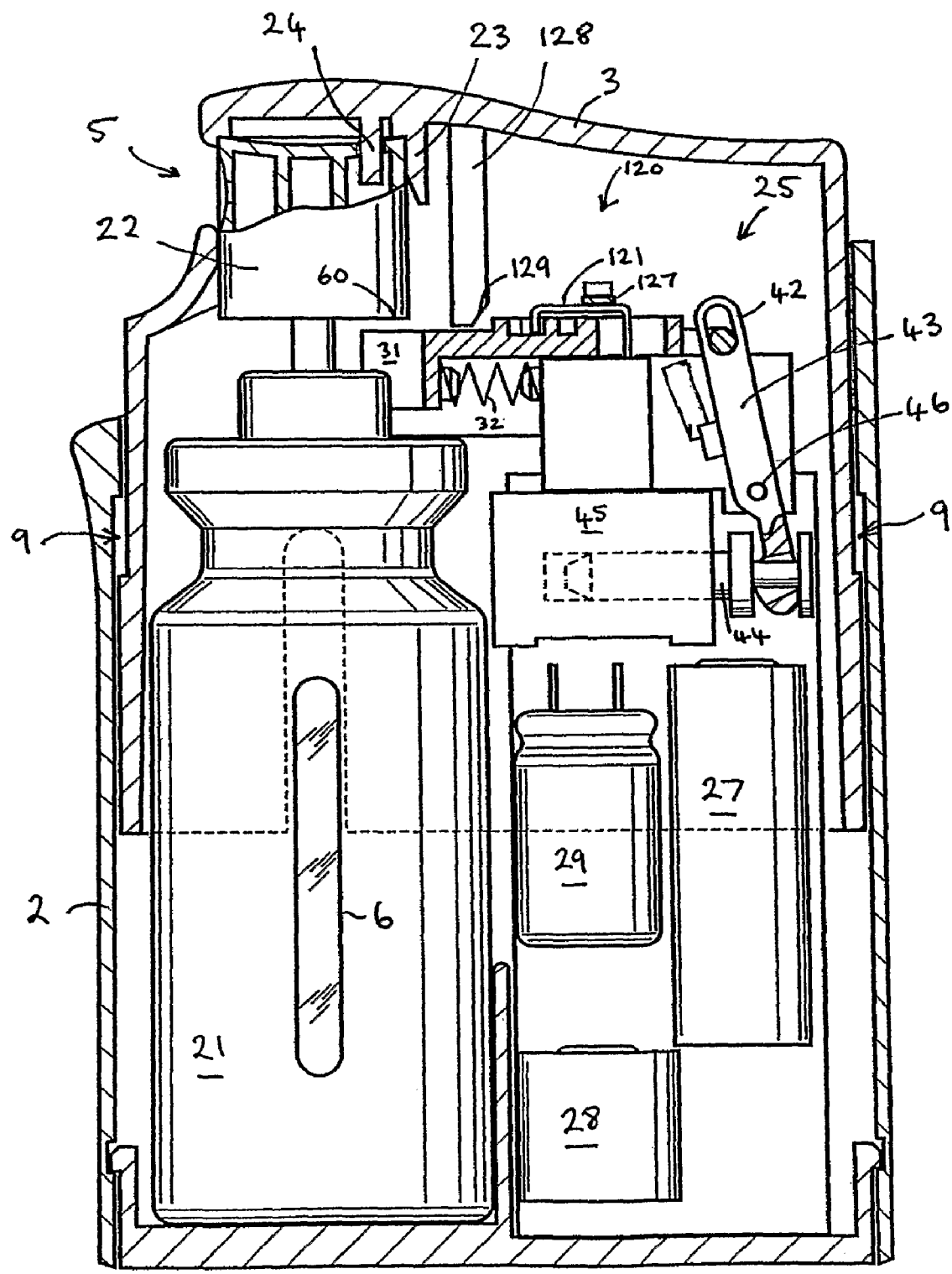
FIG. 10 is a sectional elevation of a dispensing system in accordance with a second embodiment having a push-push mechanism and showing the lock in its unlocked state.

The second embodiment differs from the first embodiment primarily in the detailed construction of the lock 25 and in certain aspects of operation of the control circuit 26. FIG. 10 is an overview.

Figure 11:
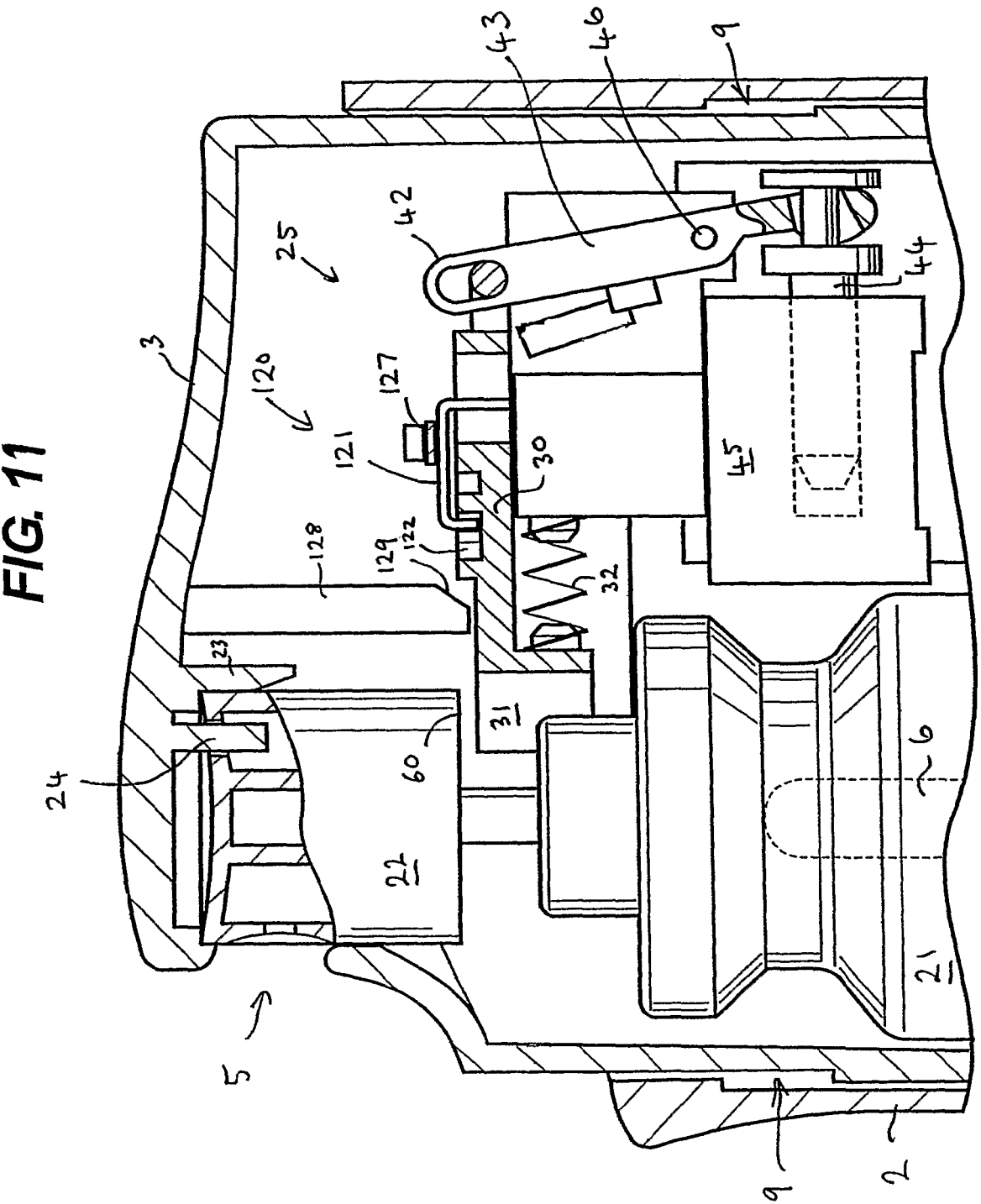
FIG. 11 is an enlarged view of the lock of FIG. 10.

As shown in enlarged view in FIG. 11, the lock 25 of the second embodiment has a locking member 30 having an end portion 31 adjacent a shoulder 60 of an actuator 22. The locking member 30 has at its other end a pivotal connection to a lever 43 which serves as a pivotal linkage between the locking member and the plunger 44 of a solenoid 45.

Figure 13:
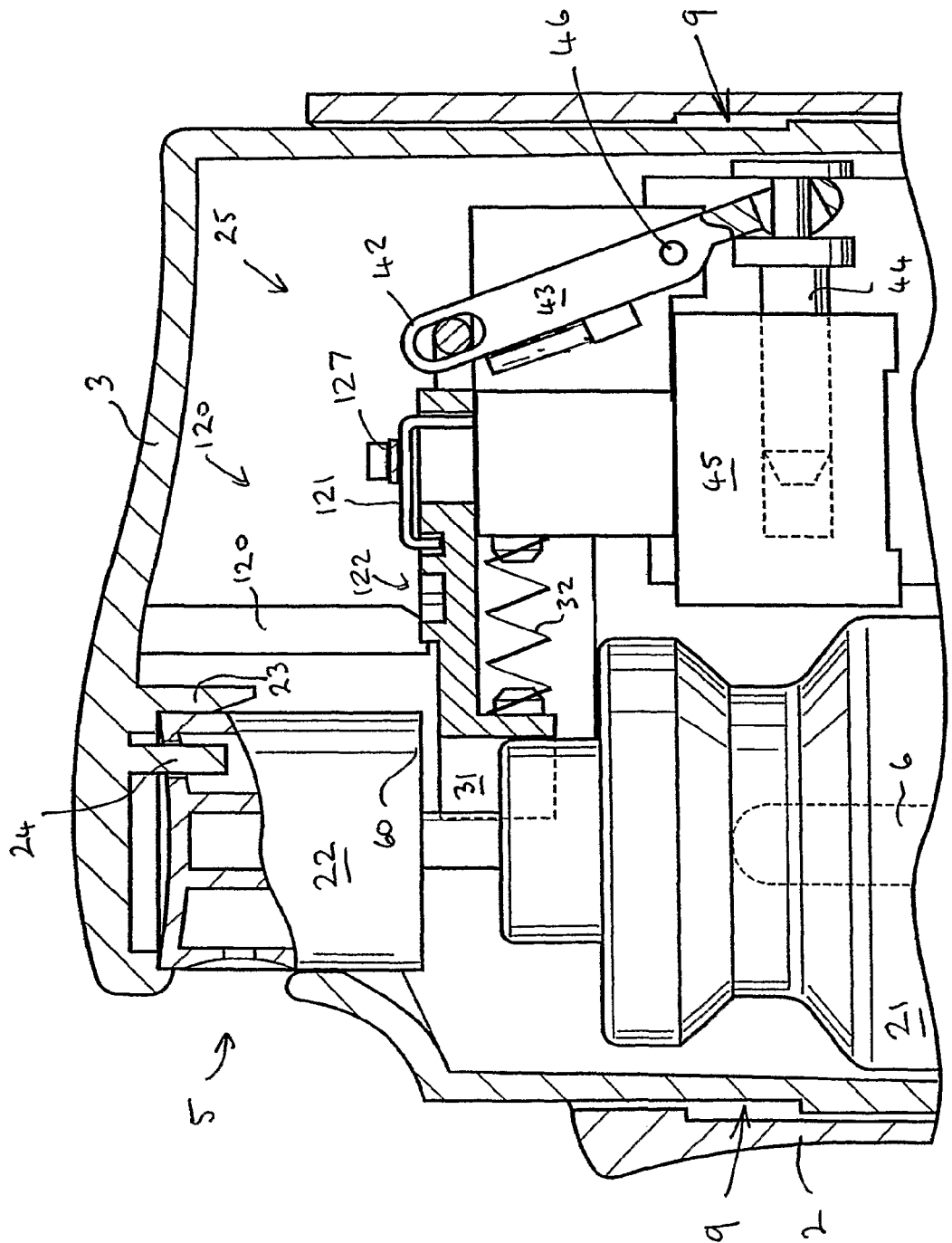
FIG. 13 is a view corresponding to FIG. 12 showing the actuator having returned to its rest position.

The locking member 30 is biased by a spring 32 towards the line of motion of the actuator 22 and, in the rest position shown in FIG. 11 in which the lock 25 is unlocked, is prevented from moving in response to the spring action by a latching mechanism 120. The latching mechanism 120 is a push-push mechanism which provides two possible stable states of the latching mechanism. The first stable state corresponds to the unlocked state of lock 25, as shown in FIG. 11. The second stable state corresponds to the locked state of the lock, as shown in FIG. 13 in which the locking member 30 is advanced to a position in which the first end portion 31 limits travel of the actuator 22 by abutment against the actuator.

The latching mechanism 120 relies upon interaction between a cam follower pin 121 and surfaces of a cam track 122. The cam follower pin 121 is resiliently biased into positive contact with the floor surfaces 126 by a leaf spring 127, as shown in FIG. 11. The cam track 122 is shown schematically in FIGS. 14 to 16, and in more detail in FIG. 17. The cam track 122 defines a closed path around which a free end 123 of the cam follower pin 121 may travel, a fixed end 124 of the cam follower pin remaining stationary and such that the position of the locking member 30 relative to the actuator 22 is determined by the instantaneous location of the free end 123 relative to the track.

Figure 14:
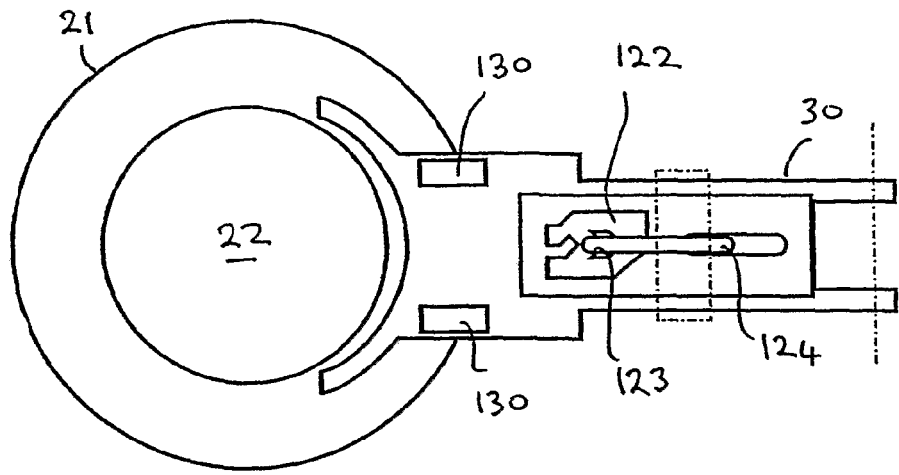
FIG. 14 is a plan view showing detail of the push-push mechanism in the unlocked state of the lock.
Figure 16:
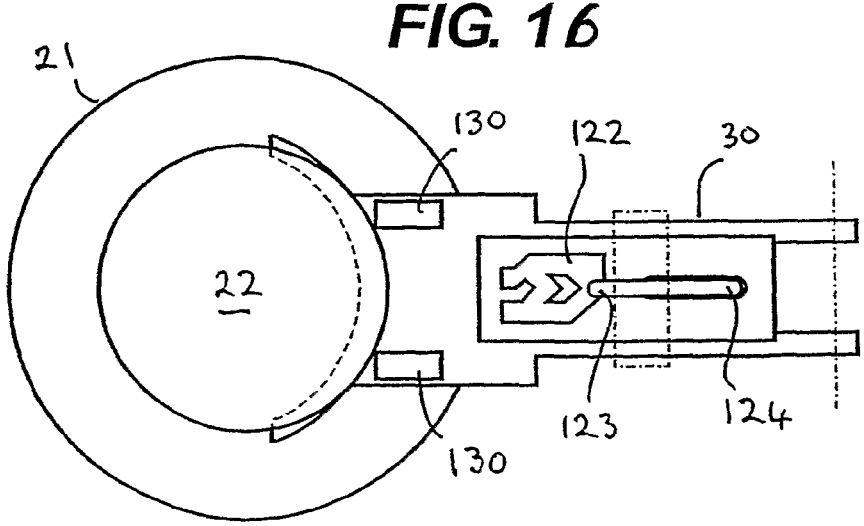
FIG. 16 is a corresponding view showing the push-push mechanism in the locked state.

The cam track 122 defines two stable positions of the free end 123. The first position corresponding to the unlocked state is shown in FIG. 14, and the second position corresponding to the locked state is shown in FIG. 16.

As illustrated schematically in FIG. 17, the cam track 122 is defined by side-walls 125 and ramped floor surfaces 126, the floor surfaces being ramped in ratchet-like manner to permit travel of the free end 123 of the cam follower pin 121 in one fixed direction around the closed path circuit, so that back-tracking is not possible.

Figure 15:
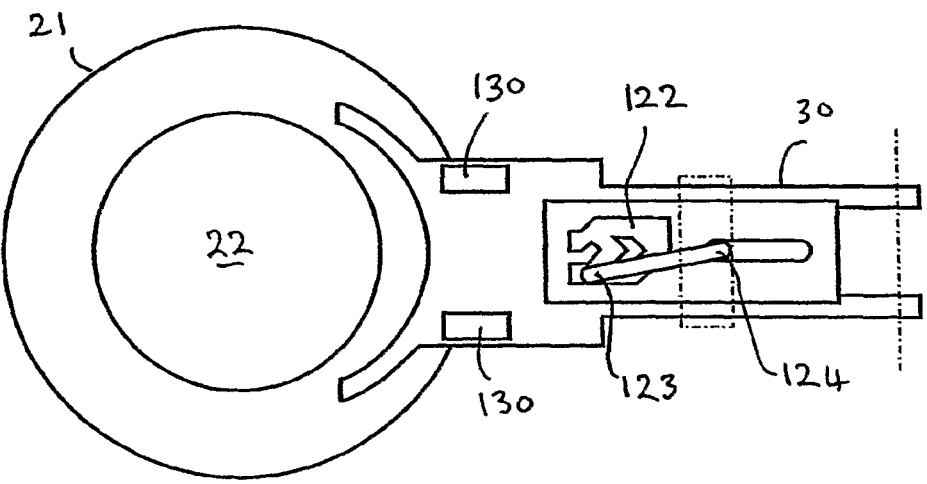
FIG. 15 is a corresponding view showing the push-push mechanism in an intermediate position.

In order for the push-push mechanism to operate, a retraction movement of the locking member 30 (i.e. to the right as drawn) is first required in order to place the free end 123 in an intermediate portion of the cam track 122, and a subsequent forward movement of the locking member 30 (i.e. to the left) which continues until the next available stable state of the push-push mechanism is reached. As shown in FIGS. 14 to 16, the retraction movement (to the right) may be initiated either by energisation of the solenoid 45 or by mechanical impetus originating from depression of the button 3, as described below. Subsequent forward movement (to the left) is effected by action of spring 32.

Referring to FIG. 11, the dispenser of the second embodiment is shown in its rest state, in which the lock 25 is in an unlocked state and the button 3 is fully raised. In this position, the end portion 31 of the locking member 30 is retracted so as to provide no limit against downward travel of the actuator 22, since there is a defined radial clearance between the shoulder 60 of the actuator and the end portion.

The button 3 has a pair of legs 128, each being chamfered at its lower end to provide a cam surface 129. In the rest position, as shown in FIG. 11, the legs 128 remain clear of the locking member 30. In this configuration, the looking member 30 is restrained from forward motion towards the actuator 22 by the cam follower pin 121 co-operating with the cam track 122, as shown in FIG. 14.

When it is required to dispense a dose, the button 3 is manually depressed, thereby initiating downward travel of the actuator 22 towards the container 21. The legs 128 move towards and come into contact with the locking member 30 and cam action occurs between the cam surfaces 129 and an upper edge of the locking member 30, with a resulting movement of the locking member 30 in a direction away from the actuator 22. The locking member 30 is thus retracted by cam action and moves to a position shown in FIG. 15, in which retraction (movement to the right of FIG. 15) of the locking member 30 is accompanied by travel of the free end 123 of the cam follower 121 within the cam track 122 to an intermediate position, as shown in FIG. 15.

Figure 12:
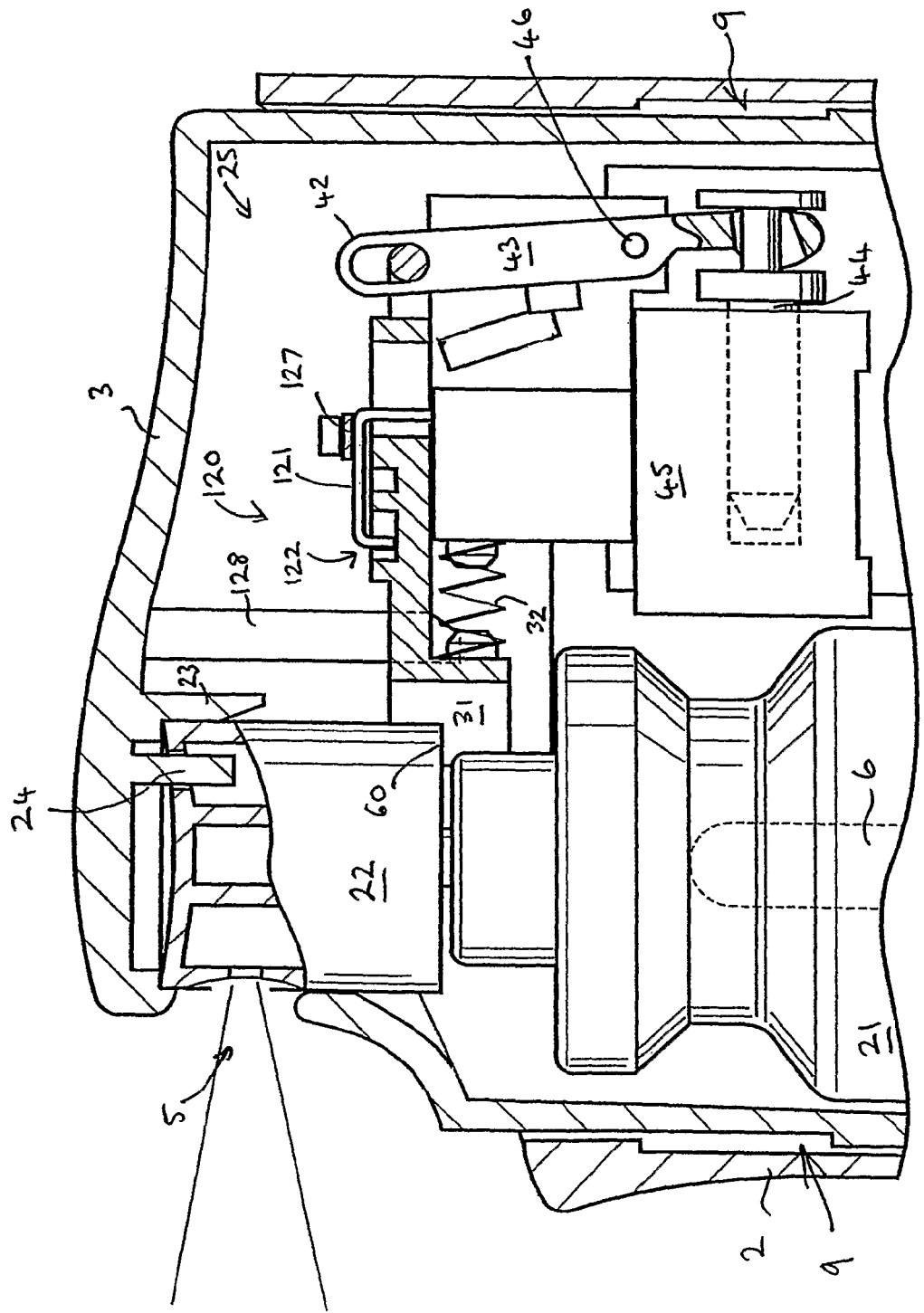
FIG. 12 is a view corresponding to FIG. 11 showing the actuator fully depressed and dispensing a dose.

The dose is then dispensed, as shown in FIG. 12, and the button is released so as to rise towards its rest position. During this initial movement, the legs 128 project through apertures 130 in the locking member 30, as shown in FIGS. 14 to 16, and the presence of the legs within the aperture prevents further movement of the locking member 30.

When the button position rises to the extent that the shoulder 60 of actuator 22 is clear of the end portion 31 and legs 128 rise clear of the apertures 130, the locking member 30 is released from this restraint. By action of spring 32, the position of the locking member 30 advances towards the actuator 22 and comes to rest in the locked position of FIG. 16, where the latching mechanism 120 is in its second stable state with the free end 123 of the cam follower resisting further advancement of the locking member.

The lock 25 is now in a locked state, as shown in FIG. 13, in which the end portion 31 of the locking member 30 is located so as to limit travel of the actuator 22 and thereby prevent completion of any dispensing stroke.

In this locked state, the position of the lever 43 is such that contact between the contact pins and the contact 49 is made. This signals to the control circuit 26 that the lock is in its locked state.

The control circuit 26 then initiates determination of a lock-out period during which no further actuation of the dispenser is to be allowed. At the end of the lock-out period, the control circuit energises the solenoid 45 such that the plunger 44 is pulled into the solenoid, this motion being communicated via lever 43 to apply a retracting impetus to the locking member 30. The solenoid is then de-energised, allowing the locking member 30 to relax to a new stable state, corresponding to the configuration of FIG. 14 in which the lock is now placed in an unlocked state.

Any further actuation of the dispenser will result in a repeat of the above sequence, in which the lock 25 is automatically self-locking after each dose is dispensed and subsequently unlocked only by firing of the solenoid by the control circuit 26.

The control circuit 26 may additionally or alternatively be configured to provide a dosing schedule in which, if a further dose is not taken within a predetermined time interval from unlocking the lock 25, the control circuit energises the solenoid 45 again in order to initiate a further lock-out period. By energising the solenoid 45, an impetus is applied to retract the locking member 30, as shown in FIG. 15, so that, when the solenoid is de-energised, the locking member relaxes to a new locked state, as shown in FIG. 16. This state will continue until the control circuit 26 again energises the solenoid 45 to change the state of the latching mechanism 120 to place the lock in an unlocked state.

In the second embodiment, unlike the first embodiment, the control circuit 26 is able not only to unlock the lock 25 but also to relock it, simply by energising the solenoid 45.

In one example, after an initial dispensing stroke, the control circuit 26 determines a first lock-out period of four seconds, immediately following which the solenoid is energised to change the state of the lock into an unlocked state. A dose allowance period is then defined, e.g. of 15 minutes from the change of state. If a further dispensing stroke occurs within this dose allowance period, self-locking action will return the lock to its locked state and the control circuit 26 will then determine a second lock-out period, e.g. of 2 hours, before again energising the solenoid to return the lock to its unlocked state.

However, if no dispensing stroke occurs during the dose allowance period, the control circuit 26 energises the solenoid at the end of the second lock-out period, to return the lock to its locked state for a further lock-out period, e.g. of 1 hour 45 minutes. The control circuit 26 then energises the solenoid, to return the lock to its unlocked state to permit further doses to be dispensed.

Other patterns of similar or greater complexity may be devised and embodied in the control circuit 26 in accordance with a required dosing schedule.

The control circuit 26 is required to energise the solenoid 45 only during transitions from one state to another, thereby minimising the drain on the current resources available to the control circuit and extending battery life. The sensor similarly draws current only when the locked state of the lock 25 is sensed.

In each of the first and second embodiments, the control circuit 26 may optionally include a failsafe feature whereby, after each energisation of the solenoid 45, the status of the sensor is determined and compared with the expected status of the sensor. For example, in the first embodiment, after each energisation of the solenoid 45, the lock 25 should transit from the locked state to the unlocked state. If the sensor nevertheless indicates that the lock remains in the locked state, this can be interpreted by the control circuit 26 as being a fault condition. Remedial action implemented by the control circuit 26 may be to energise the solenoid 45 repeatedly, until the required status of the sensor is detected. A maximum number of repeat attempts may be set by the control circuit 26, following which the control circuit may enter a failsafe mode in which no further energising of the solenoid 45 is permitted.

In the second embodiment, after each energisation of the solenoid 45, the status of the sensor should change to correspond to either the locked or unlocked state of the lock 25, depending upon the initial state of the lock prior to energising the solenoid. If no transition of state has occurred, a defect condition may then be determined to exist by the control circuit 26 and appropriate remedial action taken, as indicated above.

A dispenser of the invention may include visual indicators provided on the side edge of the locking member 30, at a position in which allows the position of the locking member to be determined by inspection through the port 7 shown in FIG. 1. For example, red and green dots may be applied to the locking member so that a green dot when visible indicates an unlocked state and a red dot when visible indicates a locked state.

In each of the above embodiments, the control circuit 26 consists of a printed circuit board on which are mounted a microprocessor, the solenoid 45, the contact pins, and the contact 49 together with capacitor 29 and peripheral components. The microprocessor is preferably programmed with deterministic software for regulating the timing of unlocking the lock 25 and, in the case of the second embodiment, optionally relocking the lock by energising the solenoid 45.

A dispenser of the invention may include means to enable the microprocessor to be reprogrammed in accordance with a new dosing schedule. The control circuit may store a dispensing history of the device which may be subsequently downloaded for analysis.

In each of the above embodiments, the mass of the locking member is selected to dynamically balance the mass of the solenoid plunger such that, when the system is subject to shock or impact, the effect of inertia on the locking member and the solenoid is to apply substantially equal and opposite turning moments about the pivot pin 46, so that there is minimal net turning moment applied to the locking member. The spring 32 provides sufficient restraint to prevent any net movement of the locking member. Inadvertent change of state of the lock is thereby avoided, when the system is subject to accidental or deliberate shocks and impacts.

A number of variations to the disclosed embodiments are envisaged. For example, the actuator 22 and button 3 may be formed integrally. The applicator 4 may be modified to be suitable for other forms of delivery such as inhalation therapy. Alternatively, the button may be constructed so as to be connectable to a number of alternative applicators.

The dispenser may comprise a pump dispenser, particularly where low velocity aerosol delivery is required, as in the case of sublingual delivery, or alternatively may comprise a pressurised dispensing container, particularly where higher velocity aerosols are required, such as in the case of inhalation therapy.

Other forms of sensor may be used to sense the locking state of the lock. For example, the position of the locking member itself may be sensed or alternatively the position of the solenoid plunger. Sensing may be via the use of electrical contacts which are bridged to complete a circuit. Alternatively, different forms of sensor for measuring position or proximity may be utilised.

In the specific description of the embodiments, reference is made to springs providing bias and motion where required. Alternative spring construction may be used. For example, tension springs may be used instead of compression springs and leaf springs may be used instead of coil springs. Other resilient means including the use of magnets may be substituted where appropriate.

In the embodiment illustrated in FIG. 1, indicator port 7 is provided in the button. Alternatively, the indicator port may be provided in the housing, depending upon the shapes adopted for the housing and top button and the relative position of the components of the lock 25.

In the embodiments disclosed above, the lock 25 engages a surface of the actuator 22. Alternative embodiments are envisaged in which actuator movement is limited by the lock engaging a feature formed in the button 3, such embodiments being equally effective since the button 3 and actuator 22 move in unison throughout the stoke of the dispenser.

In the arrangement of FIG. 2, the container 21 rests upon the chassis 10 which forms an end portion of the housing 2. Dispensers of different length may be accommodated, e.g. by including a modification to the chassis 10 to provide a support so that the bottom end of the container stands off from the base of the housing.

The embodiments detailed above have two separate batteries. By appropriate modification to the circuit, a single battery may be utilised.

The invention claimed is:

1. A dispenser suitable for biomedical use, comprising: an actuator, wherein movement comprising completion of a dispensing stroke of the actuator dispenses a dose of a product; a lock; first retaining means for retaining the lock in an unlocked state prior to a dispensing stroke; second retaining means for retaining the lock in a locked state after a dispensing stroke has been completed; a lock actuator operable when energized to change the state of the lock; and a control circuit operable to energise the lock actuator; wherein the first and second retaining means are operable independently of the lock actuator so that the lock actuator is required to be energised only when changing the state of the lock; and wherein the lock comprises a locking member movable between a retracted position in the unlocked state and, in the locked state, an advanced position at which the locking member defines a limit of travel of the actuator, and wherein the device further comprises a self-locking mechanism comprising a resilient means biasing the locking member into the advanced position; and wherein the self-locking mechanism comprises a latch operable to hold the locking member in the retracted position in the unlocked state and a latch release mechanism operable to release the latch in response to movement of the actuator to a position beyond the limit of actuator travel defined by the locking member in the locked state.

2. The dispenser as claimed in claim 1, wherein the actuator comprises a contact surface against which the locking member is slidable when released by the latch to maintain the locking member at a position intermediate the retracted position and the advanced position until the actuator returns during a return stroke after dispensing a dose to a position within the limit of actuator travel in the locked state, thereafter allowing the locking member to reach the advanced position.

3. The dispenser as claimed in claim 1, wherein the lock comprises a push-push mechanism defining a first stable position of the locking member corresponding to the locked state and a second stable position of the locking member corresponding to the unlocked state, the push-push mechanism further comprising resilient means operable such that, when the locking member is displaced from one of the stable positions, the resilient means biases the locking member into the other of the stable positions.

4. The dispenser as claimed in claim 3, comprising a formation connected to the actuator and operable to displace the locking member from the second stable position during a dispensing stroke of the actuator, whereby the locking member is returned to the first stable position by action of the resilient means during the return stroke of the actuator.

5. The dispenser as claimed in claim 3, comprising a linkage operable to link the lock actuator to the push-push mechanism for displacing the locking member from a stable position when the lock actuator is energised, whereby the resilient means is operable to return the locking member thereafter to a different stable position.

6. The dispenser as claimed in claim 1, comprising a housing and a button formation cooperating with and displaceable relative to the housing to move in unison with the actuator during dispensing and return strokes of the actuator, wherein the button formation and the actuator have cooperating alignment formations.

7. The dispenser as claimed in claim 6, wherein the housing includes a first viewing aperture through which the presence and/or amount of product to be dispensed may be inspected.

8. The dispenser as claimed in claim 6, which includes a second viewing aperture, and the lock comprises indicia, viewable through the second viewing aperture, that indicate whether the lock is in the locked or the unlocked state.

9. The dispenser as claimed in claim 1, which comprises a drug formulation to be dispensed.

10. A dispenser suitable for biomedical use, comprising:
an actuator, wherein movement comprising completion of a dispensing stroke of the actuator dispenses a dose of a product;
a lock operable in a locked state to limit the actuator movement so as to prevent a dose from being dispensed, wherein the lock has a resilient self-locking mechanism for placing the lock into the locked state after a dose is dispensed and a sensor operable to sense when the lock is in the locked state;
a lock actuator; and
a control circuit responsive to the sensor and operable after a lock-out period determined by the control circuit to energise the lock actuator to return the lock to an unlocked state,
wherein said dispenser further comprises a means for engaging and holding the lock as it returns to the unlocked state, and which is disengaged from the lock during a dispensing state; and
wherein the lock comprises a locking member movable between a retracted position in the unlocked state and, in the locked state an advanced position at which the locking member defines a limit of travel of the actuator, and wherein the self-locking mechanism comprises a resilient means biasing the locking member into the advanced position; and wherein the self-locking mechanism comprises a latch operable to hold the locking member in the retracted position in the unlocked state and a latch release mechanism operable to release the latch in response to movement of the actuator to a position beyond the limit of actuator travel defined by the locking member in the locked state.

11. The dispenser as claimed in claim 10, wherein the actuator comprises a contact surface against which the locking member is slidable when released by the latch to maintain the locking member at a position intermediate the retracted position and the advanced position until the actuator returns during a return stroke after dispensing a dose to a position within the limit of actuator travel in the locked state, thereafter allowing the locking member to reach the advanced position.

12. The dispenser as claimed in claim 10, wherein the lock comprises a push-push mechanism defining a first stable position of the locking member corresponding to the locked state and a second stable position of the locking member corresponding to the unlocked state, the push-push mechanism further comprising resilient means operable such that, when the locking member is displaced from one of the stable positions, the resilient means biases the locking member into the other of the stable positions.

13. The dispenser as claimed in claim 12, comprising a formation connected to the actuator and operable to displace the locking member from the second stable position during a dispensing stroke of the actuator, whereby the locking member is returned to the first stable position by action of the resilient means during the return stroke of the actuator.

14. The dispenser as claimed in claim 12, comprising a linkage operable to link the lock actuator to the push-push mechanism for displacing the locking member from a stable position when the lock actuator is energised, whereby the resilient means is operable to return the locking member thereafter to a different stable position.

15. The dispenser as claimed in claim 10, comprising a housing and a button formation cooperating with and displaceable relative to the housing to move in unison with the actuator during dispensing and return strokes of the actuator, wherein the button formation and the actuator have cooperating alignment formations.

16. The dispenser as claimed in claim 15, wherein the housing includes a first viewing aperture through which the presence and/or amount of product to be dispensed may be inspected.

17. The dispenser as claimed in claim 15, which includes a second viewing aperture, and the lock comprises indicia, viewable through the second viewing aperture, that indicate whether the lock is in the locked or the unlocked state.

18. The dispenser as claimed in claim 10 which comprises a drug formulation to be dispensed.

19. A dispenser suitable for biomedical use, comprising:
an actuator, wherein movement comprising completion of a dispensing stroke of the actuator dispenses a dose of a product;
a lock operable in a locked state to limit the actuator movement so as to prevent a dose from being dispensed, wherein the lock has a resilient self-locking mechanism for placing the lock into the locked state after a dose is dispensed and a sensor operable to sense when the lock is in the locked state;
a lock actuator; and
a control circuit responsive to the sensor and operable after a lock-out period determined by the control circuit to energise the lock actuator and return the lock to an unlocked state,
wherein the dispenser further comprises a solenoid and a capacitor, and the control circuit applies a charging voltage to the capacitor and, after a suitable charging period, connects the output voltage to the solenoid, to deliver a current pulse for activation of the solenoid, whereby the lock actuator is energized and the lock is returned to the unlocked state and may be maintained in the unlocked state for an indefinite period without energy consumption, and wherein the sensor draws current only when the lock is in the locked state; wherein the self-locking mechanism comprises a latch operable to hold the locking member in the retracted position in the unlocked state and a latch release mechanism operable to release the latch in response to movement of the actuator to a position beyond the limit of actuator travel defined by the locking member in the locked state.

20. The dispenser as claimed in claim 19, wherein the self-locking mechanism comprises a latch operable to hold the locking member in the retracted position in the unlocked state and a latch release mechanism operable to release the latch in response to movement of the actuator to a position beyond the limit of actuator travel defined by the locking member in the locked state.

21. The dispenser as claimed in claim 20, wherein the actuator comprises a contact surface against which the locking member is slidable when released by the latch to maintain the locking member at a position intermediate the retracted position and the advanced position until the actuator returns during a return stroke after dispensing a dose to a position within the limit of actuator travel in the locked state, thereafter allowing the locking member to reach the advanced position.

22. The dispenser as claimed in claim 19, wherein the lock comprises a push-push mechanism defining a first stable position of the locking member corresponding to the locked state and a second stable position of the locking member corresponding to the unlocked state, the push-push mechanism further comprising resilient means operable such that, when the locking member is displaced from one of the stable positions, the resilient means biases the locking member into the other of the stable positions.

23. The dispenser as claimed in claim 22, comprising a formation connected to the actuator and operable to displace the locking member from the second stable position during a dispensing stroke of the actuator, whereby the locking member is returned to the first stable position by action of the resilient means during the return stroke of the actuator.

24. The dispenser as claimed in claim 22, comprising a linkage operable to link the lock actuator to the push-push mechanism for displacing the locking member from a stable position when the lock actuator is energised, whereby the resilient means is operable to return the locking member thereafter to a different stable position.

25. The dispenser as claimed in claim 19, comprising a housing and a button formation cooperating with and displaceable relative to the housing to move in unison with the actuator during dispensing and return strokes of the actuator, wherein the button formation and the actuator have cooperating alignment formations.

26. The dispenser as claimed in claim 25, wherein the housing includes a first viewing aperture through which the presence and/or amount of product to be dispensed may be inspected.

27. The dispenser as claimed in claim 25, which includes a second viewing aperture, and the lock comprises indicia, viewable through the second viewing aperture, that indicate whether the lock is in the locked or the unlocked state.

28. The dispenser as claimed in claim 19 which comprises a drug formulation to be dispensed.

29. A method for dispensing a drug formulation wherein said method comprises administering the drug formulation to a patient using a dispenser selected from the group consisting of:
  a. a dispenser suitable for biomedical use, comprising: an actuator, wherein movement comprising completion of a dispensing stroke of the actuator dispenses a dose of a product; a lock; first retaining means for retaining the lock in an unlocked state prior to a dispensing stroke; second retaining means for retaining the lock in a locked state after a dispensing stroke has been completed; a lock actuator operable when energized to change the state of the lock; and a control circuit operable to energise the lock actuator; wherein the first and second retaining means are operable independently of the lock actuator so that the lock actuator is required to be energised only when changing the state of the lock; and wherein the lock comprises a locking member movable between a retracted position in the unlocked state and, in the locked state, an advanced position at which the locking member defines a limit of travel of the actuator, and wherein the device further comprises a self-locking mechanism comprising a resilient means biasing the locking member into the advanced position; and wherein the self-locking mechanism comprises a latch operable to hold the locking member in the retracted position in the unlocked state and a latch release mechanism operable to release the latch in response to movement of the actuator to a position beyond the limit of actuator travel defined by the locking member in the locked state;
  b. dispenser suitable for biomedical use, comprising:
  an actuator, wherein movement comprising completion of a dispensing stroke of the actuator dispenses a dose of a product;
  a lock operable in a locked state to limit the actuator movement so as to prevent a dose from being dispensed, wherein the lock has a resilient self-locking mechanism for placing the lock into the locked state after a dose is dispensed and a sensor operable to sense when the lock is in the locked state;
  a lock actuator; and
  a control circuit responsive to the sensor and operable after a lock-out period determined by the control circuit to energise the lock actuator to return the lock to an unlocked state,
  wherein said dispenser further comprises a means for engaging and holding the lock as it returns to the unlocked state, and which is disengaged from the lock during a dispensing state; and
  wherein the lock comprises a locking member movable between a retracted position in the unlocked state and, in the locked state, an advanced position at which the locking member defines a limit of travel of the actuator, and wherein the self-locking mechanism comprises a resilient means biasing the locking member into the advanced position; and wherein the self-locking mechanism comprises a latch operable to hold the locking member in the retracted position in the unlocked state and a latch release mechanism operable to release the latch in response to movement of the actuator to a position beyond the limit of actuator travel defined by the locking member in the locked state; and
  c. a dispenser suitable for biomedical use, comprising:
  an actuator, wherein movement comprising completion of a dispensing stroke of the actuator dispenses a dose of a product;
  a lock operable in a locked state to limit the actuator movement so as to prevent a dose from being dispensed, wherein the lock has a resilient self-locking mechanism for placing the lock into the locked state after a dose is dispensed and a sensor operable to sense when the lock is in the locked state;
  a lock actuator; and
  a control circuit responsive to the sensor and operable after a lock-out period determined by the control circuit to energise the lock actuator and return the lock to an unlocked state,
  wherein the dispenser further comprises a solenoid and a capacitor, and the control circuit applies a charging voltage to the capacitor and, after a suitable charging period, connects the output voltage to the solenoid, to deliver a current pulse for activation of the solenoid, whereby the lock actuator is energized and the lock is returned to the unlocked state and may be maintained in the unlocked state for an indefinite period without energy consumption, and wherein the sensor draws current only when the lock is in the locked state; wherein the self-locking mechanism comprises a latch operable to hold the locking member in the retracted position in the unlocked state and a latch release mechanism operable to release the latch in response to movement of the actuator to a position beyond the limit of actuator travel defined by the locking member in the locked state.

* * * * *